United States Patent
Kang et al.

(10) Patent No.: US 10,639,320 B2
(45) Date of Patent: May 5, 2020

(54) PHARMACEUTICAL COMPOSITION COMPRISING GOLD-CONTAINING AGENT FOR PREVENTING OR TREATING LIVER FIBROSIS OR LIVER CIRRHOSIS

(71) Applicant: KOREA UNITED PHARM. INC., Sejong (KR)

(72) Inventors: Keon Wook Kang, Seoul (KR); Nayoun Kim, Gyeonggi-do (KR); Kyung Rok Yoon, Gyeongsangnam-do (KR)

(73) Assignee: KOREA UNITED PHARM. INC., Sejong-si (KR)

( * ) Notice: Subject to any disclaimer, the term of this patent is extended or adjusted under 35 U.S.C. 154(b) by 0 days.

(21) Appl. No.: 15/504,663

(22) PCT Filed: Aug. 20, 2015

(86) PCT No.: PCT/KR2015/008677
§ 371 (c)(1),
(2) Date: Feb. 17, 2017

(87) PCT Pub. No.: WO2016/028092
PCT Pub. Date: Feb. 25, 2016

(65) Prior Publication Data
US 2017/0266219 A1    Sep. 21, 2017

(30) Foreign Application Priority Data

Aug. 21, 2014  (KR) .......................... 10-2014-0108907
Aug. 19, 2015  (KR) .......................... 10-2015-0116396

(51) Int. Cl.
| | | |
|---|---|---|
| *A61K 31/7135* | (2006.01) | |
| *A61K 33/24* | (2019.01) | |
| *A61K 31/28* | (2006.01) | |
| *A61P 1/16* | (2006.01) | |

(52) U.S. Cl.
CPC .......... *A61K 31/7135* (2013.01); *A61K 31/28* (2013.01); *A61K 33/24* (2013.01); *A61P 1/16* (2018.01)

(58) Field of Classification Search
None
See application file for complete search history.

(56) References Cited

FOREIGN PATENT DOCUMENTS

KR          10-0949417 B1       3/2010

OTHER PUBLICATIONS

Madeira et al., "The biological activity of auranofin: implications for novel treatment of diseases", Inflammopharmacol., 2012, vol. 20, No. 6, pp. 297-306.*
Ashino et al., "Auranofin protects against cocaine-induced hepatic injury through induction of heme oxygenase-1", J.Toxicol.Sci., 2011, vol. 36, No. 5, pp. 635-643.*
Ashino et al., "Auranofin protects against cocaine-induced hepatic injury through induction of heme oxygenase-1", J.Toxicol.Sci., 2011, vol. 36, No. 5, pp. 635-643 (Year: 2011).*
Wang et al., "Inhibiting heme oxygenase-1 attenuates rat liver fibrosis by removing iron accumulation", World J. Gastroenterol., 2013, vol. 19, No. 19, pp. 2921-2934 (Year: 2013).*
Yang et al., "Heme oxygenase-1 prevents liver fibrosis in rats by regulating the expression of PPARγ and NF-κB", World J. Gastroenterol., 2012, vol. 18, No. 14, pp. 1680-1688 (Year: 2012).*
Mayo Clinic, "Cirrhosis: Diagnosis & Treatment", https://www.mayoclinic.org/diseases-conditions/cirrhosis/diagnosis-treatment/drc-20351492, accessed Mar. 30, 2019 (Year: 2019).*
The Merck Manual, "Hepatic Fibrosis", https://www.merckmanuals.com/professional/hepatic-and-biliary-disorders/fibrosis-and-cirrhosis/hepatic-fibrosis, accessed Mar. 30, 2019 (Year: 2019).*
Amitava, Das et al "Fabrication and characterization of an inorganic gold and silica nanoparticle mediated drug delivery system for nitric oxide; Fabrication and characterization of an inorganic gold and silica nanoparticle mediated drun delivery system for nitric oxide" Nanotechnology, IOP, Bristol, GB, vol. 21, No. 30, Jul. 8, 2010.
Extended European Search Report [EP 15834611.4] dated Mar. 16, 2018.
Kabir, Nurul et al., "Silymarin coated gold nanoparticles ameliorates CCL4-induced hepatic injury and cirrhosis through down regulation of hepatic stellate cells and attenuation of Kupffer cells" RSC Advances, 2014. 1, vol. 4, No. 18, pp. 9012-9020.
Das, Amitava et al. "Fabrication and characterization of an inorganic gold and silica nanoparticle mediated drug delivery system for nitric oxide" Nanotechnology, 2010, vol. 21, No. 30, Article No. 305102.
Yang, Hui et al. "Heme oxygenase-1 prevents liver fibrosis in rats by regulating the expression of PPAR gamma and NF-kappa B" World Journal of Gastroenterology, vol. 18, Issue.14, pate.1680-1688.

* cited by examiner

*Primary Examiner* — James D. Anderson
*Assistant Examiner* — Stephanie K Springer
(74) *Attorney, Agent, or Firm* — Edwin S. Flores; Daniel J. Chalker; Chalker Flores, LLP (57) ABSTRACT

The present invention relates to a pharmaceutical composition for preventing or treating liver fibrosis or liver cirrhosis, and more specifically, to a pharmaceutical composition for preventing or treating liver fibrosis or liver cirrhosis comprising a gold-containing agent. The pharmaceutical composition of the present invention, by comprising the gold-containing agent as an active ingredient, not only promotes M2-type transformation of macrophages but also inhibits the activation of stellate cells due to the increase of TREM-2 expression, and is thus expected to be effectively used as a pharmaceutical composition, a food composition, etc., for preventing, treating, or ameliorating liver fibrosis or liver cirrhosis. Additionally, gold-containing agents, such as auranofin, sodium aurothiomalate, and aurothioglucose, have long been used for the treatment of a different disease (rheumatoid arthritis), and thus they have an advantage in that they are less likely to cause adverse effects.

2 Claims, 9 Drawing Sheets

PHARMACEUTICAL COMPOSITION COMPRISING GOLD-CONTAINING AGENT FOR PREVENTING OR TREATING LIVER FIBROSIS OR LIVER CIRRHOSIS

CROSS-REFERENCE TO RELATED APPLICATIONS

This application is the National Stage of International Application No. PCT/KR2015/008677, filed on Aug. 20, 2015 claiming the priority of KR 10-2015-0116396, filed on Aug. 19, 2015, and KR 10-2014-0108907, filed on Aug. 21, 2014, the content of each of which is incorporated by reference herein.

TECHNICAL FIELD OF THE INVENTION

The present invention relates to a pharmaceutical composition for preventing or treating liver fibrosis or liver cirrhosis, and more specifically, to a pharmaceutical composition for preventing or treating liver fibrosis or liver cirrhosis including a gold-containing agent.

BACKGROUND OF THE INVENTION

The liver has a vital role in the metabolism of intracellular and extracellular materials and is a biological organ where enzyme reactions and energy metabolism occur continuously. Currently in Korea, hepatitis, liver cirrhosis, and liver cancer along with circulatory diseases account for the highest percentage among the chronic diseases, and they also belong to leading causes of death due to diseases. In particular, since Korea has a relatively high percentage of drinking population compared to those in developed countries and since heavy alcohol drinking is associated with a high risk of liver damage, Korean people are highly concerned about the seriousness of the liver-related diseases. Continuous damage in liver tissue due to viral infection or drinking can lead to liver cirrhosis or liver cancer. Considering the physiological characteristics and importance of liver tissue, it is very important to prevent and treat liver diseases. Accordingly, there is a need for the development of a pharmaceutical composition for preventing and treating liver-related diseases that can reduce damage in liver tissue and can be ultimately applicable to the treatment thereof Specifically, liver fibrosis is part of the physiological adaptive reaction accompanied by chronic liver diseases such as hepatitis, etc., and it refers to a state where the damaged liver tissue is transformed into fibrous tissue such as collagen instead of being recovered into normal liver cells. Although liver fibrosis is a physiological adaptive reaction that occurs in the course of recovering damaged tissue, the deterioration in liver function is inevitable because the liver tissue is replaced with fibrous tissue, which cannot perform at all the original functions of the liver, such as metabolism of in vivo materials, secretion of bile acid, etc. Since the continuous repetition of liver fibrosis can lead to liver cirrhosis and may cause death, it has been an important project to develop an appropriate therapeutic drug in the aspect of pharmaceutical drugs. However, the mechanism of liver fibrosis itself has not yet been clearly identified and thus the development of an appropriate therapeutic drug still remains to be solved.

Recently, it was discovered that transforming growth factor-beta (TGF-beta), which is a cytokine being freed from the macrophagic Kupffer cells and stellate cells in the liver, is an important mediator of liver fibrosis. Additionally, it was previously reported that the blocking of TGF-beta actions by TGF-beta antibody, antisense RNA thereof, and modifications of cellular TGF-beta receptors significantly inhibited the process of liver fibrosis. However, these studies were simply carried out at experimental levels and clinically-applicable pharmaceutical drugs are still not available.

As described above, it has been a major project to develop effective therapeutic agents for the treatment of liver fibrosis or liver cirrhosis and related studies have been carried out (Korean Patent No. 10-0949417) but the progress is still too slow.

SUMMARY OF THE INVENTION

Accordingly, the present invention has been made keeping in mind the above problems occurring in the prior art, and an object of the present invention is to provide a pharmaceutical composition for preventing or treating liver fibrosis or liver cirrhosis including a gold-containing agent as an active ingredient.

However, an object to be accomplished by the invention is not limited to the above-mentioned object, and other objects not mentioned above will be clearly understood by those skilled in the art from the following description.

An object of the present invention is to provide a pharmaceutical composition for preventing or treating liver fibrosis or liver cirrhosis including a gold-containing agent as an active ingredient.

In an exemplary embodiment of the present invention, the gold-containing agent may be at least one selected from the group consisting of auranofin, sodium aurothiomalate, aurothioglucose, sodium aurothiosulfate, and disodium aurothiomalate.

In another exemplary embodiment of the present invention, the composition may promote the transformation into M2-type macrophages.

In still another exemplary embodiment of the present invention, the composition may increase the expression of triggering receptor expressed on myeloid cells 2 (TREM-2).

Additionally, the present invention provides a health functional food composition for preventing or ameliorating liver fibrosis or liver cirrhosis comprising a gold-containing agent as an active ingredient.

In an exemplary embodiment of the present invention, the gold-containing agent may be at least one selected from the group consisting of auranofin, sodium aurothiomalate, aurothioglucose, sodium aurothiosulfate, and disodium aurothiomalate.

Furthermore, the present invention provides a method for treating liver fibrosis or liver cirrhosis comprising administering a gold-containing agent to a subject.

Additionally, the present invention provides a use of the gold-containing agent in the preparation of a medicament for preventing or treating liver fibrosis or liver cirrhosis.

The pharmaceutical composition of the present invention, by including a gold-containing agent as an active ingredient, not only promotes M2-type transformation of macrophages but also inhibits the activation of stellate cells due to the increase of TREM-2 expression, and is thus expected to be effectively used as a pharmaceutical composition, a food composition, etc., for preventing, treating, or ameliorating liver fibrosis or liver cirrhosis.

Additionally, gold-containing agents, such as auranofin, sodium aurothiomalate, and aurothioglucose, have long been used for treating a different disease (rheumatoid arthritis) and thus they have an advantage in that they are less likely to cause adverse effects. Furthermore, the gold-containing agents are expected to be effective for the treatment of other diseases caused by fibrosis such as renal fibrosis.

DETAILED DESCRIPTION OF THE INVENTION

With respect to the process of liver fibrosis, it was the destruction of liver cells and the action of stellate cells which recover the destroyed liver cells via collagen formation that has drawn the attention of many researchers. However, the present invention is focused on the Kupffer cells which have a macrophage function in the liver cells and the actions of bone marrow-derived macrophages that penetrate into the bloodstream.

Figure 1:
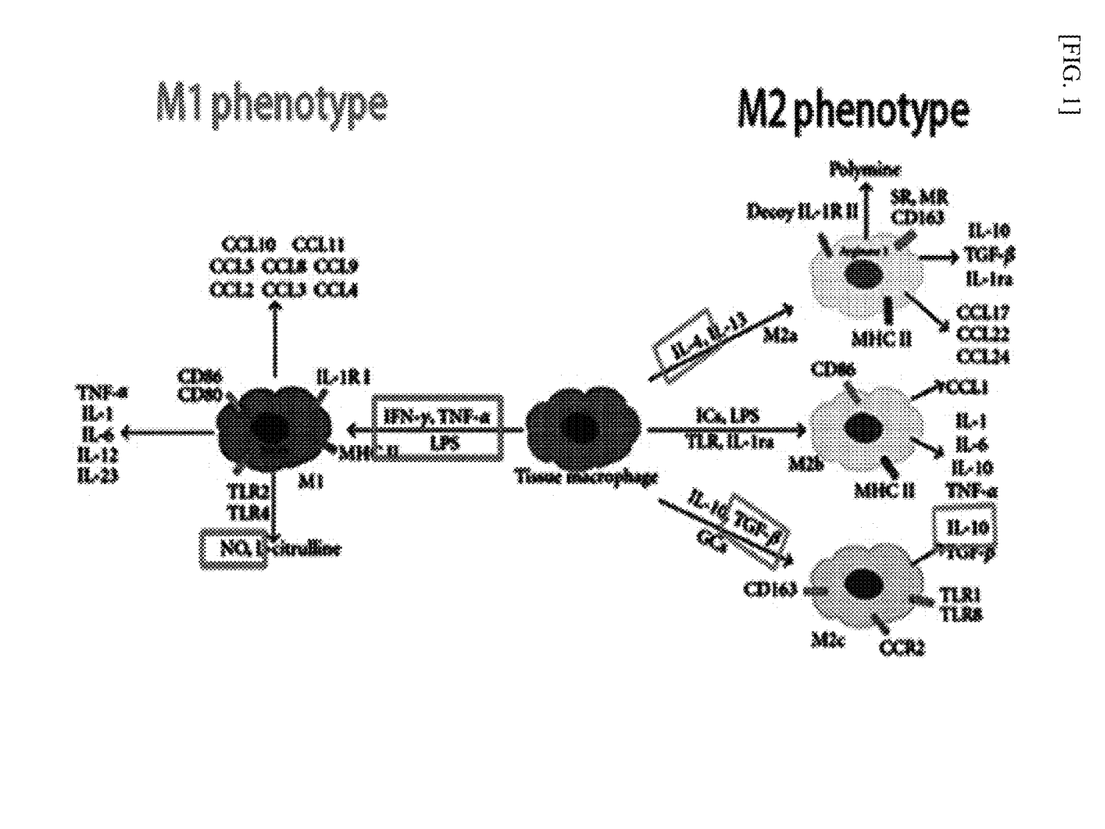
FIG. 1 shows a schematic diagram illustrating the M1/M2 transformation characteristics of macrophages and cytokines being induced therefrom.

Macrophages can broadly be divided into two phenotypes according to their differentiation process. M1-type macrophages are mostly produced by the stimulation of lipopolysaccharide (LPS), which is an endotoxin derived from bacteria, and interferon-gamma (IFN-gamma). M1-type macrophages are known to be involved in phagocytosis and accompanying amplification of inflammatory responses thereof, which arethe characteristic function of macrophages, by inducing tumor necrosis factor-alpha (TNF-alpha), interleukin-6 (IL-6), and inducible nitric oxide synthase (iNOS), whereas M2-type macrophages, which are produced by secretion of interleukin-4 (IL-4), TGF-beta, etc., induce anti-cytokines, such as IL-10, and arginase, and they are known to be involved in reactions such as tissue recovery, etc. (see FIG. 1).

A recent report revealed that M1/M2 transformation affects the fibrosis signaling. According to other reports, the aggravation of inflammation progress by M1 macrophages aggravated fibrosis, and M2 macrophages inhibited Th2 inflammatory responses and renal fibrosis via expression of arginase-1. Accordingly, it may be possible to use a pharmaceutical drug, which can appropriately control the M1/M2 transformation, for the purpose of preventing and treating liver fibrosis and liver cirrhosis.

Under the circumstances, the present inventors have made many efforts to develop a pharmaceutical drug which can appropriately control the M1/M2 transformation. As a result, they have first discovered that gold-containing agents which had been used for a different use, can inhibit liver fibrosis by transformation of macrophages into M2-type and increasing the expression of triggering receptor expressed on myeloid cells 2 (TREM-2) thereby completing the present invention.

Hereinafter, the present invention will be described in more detail.

The present invention provides a pharmaceutical composition for preventing or treating liver fibrosis or liver cirrhosis comprising a gold-containing agent as an active ingredient.

As used herein, the term "prevention" refers to all activities that inhibit or delay the occurrence of liver fibrosis or liver cirrhosis by administering the pharmaceutical composition of the present invention.

As used herein, the term "treatment" refers to all activities that improve or advantageously change the symptoms of liver fibrosis or liver cirrhosis by administering the pharmaceutical composition of the present invention.

Figure 2:
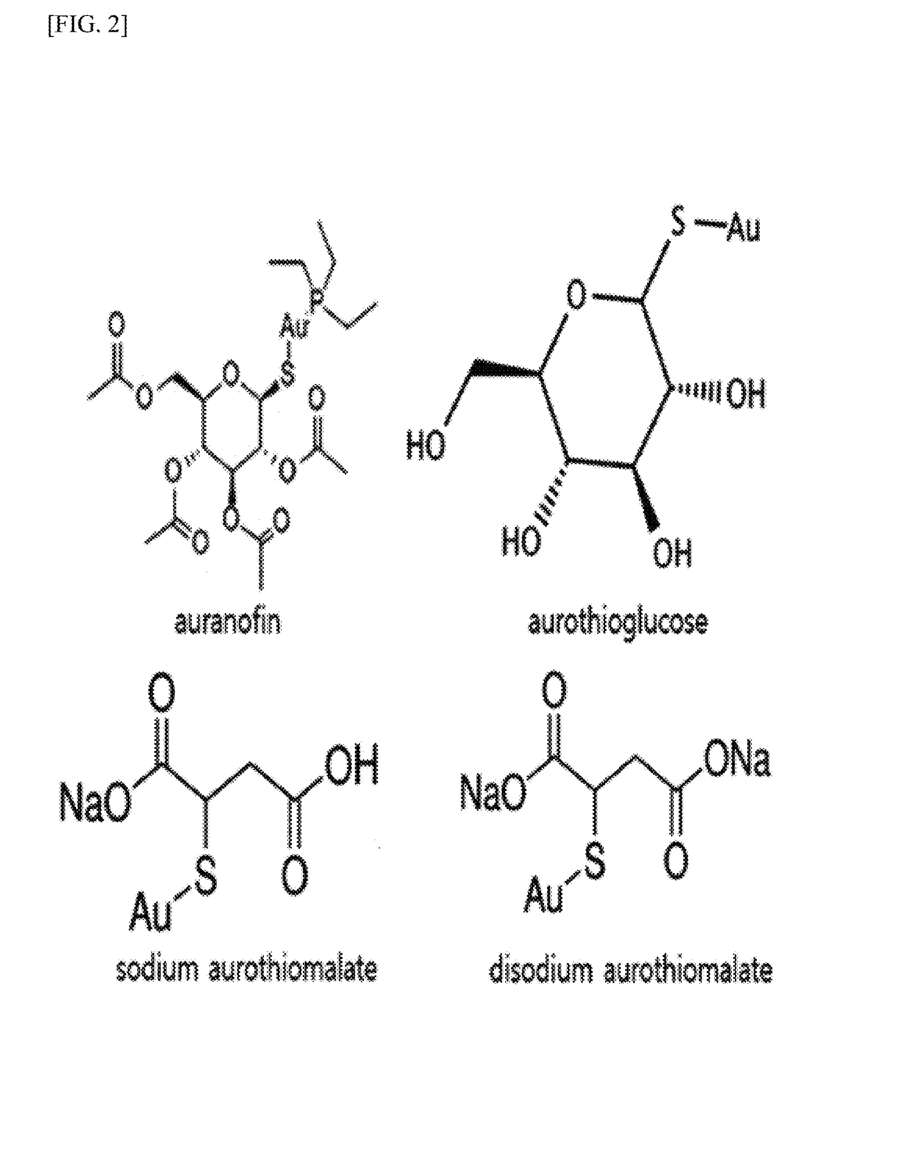
FIG. 2 shows various chemical structures of gold-containing agents.

As used herein, the term "gold-containing agent" refers to a compound, in which gold and other elements (components) are comprised in a predetermined ratio, i.e., a gold compound, and it may include both a gold (I) compound and a gold (III) compound. Examples of the gold-containing agent to be used in the present invention may include auranofin (2,3,4,6-tetra-O-acetyl-1-thio-β-D-glucopyranosato-S-[triethylphosphine] gold), sodium aurothiomalate, aurothioglucose, sodium aurothiosulfate, disodium aurothiomalate, etc., but are not limited thereto (see FIG. 2), and preferably auranofin, sodium aurothiomalate, or aurothioglucose may be used, and most preferably auranofin.

The pharmaceutical composition of the present invention, by including a gold-containing agent as an active ingredient, can not only promote M2-type transformation of macrophages but also inhibit the activation of stellate cells due to the increase of TREM-2 expression and is thereby capable of preventing, treating, or ameliorating liver fibrosis or liver cirrhosis.

In an exemplary embodiment of the present invention, it was examined whether gold-containing agents can cause transformation of macrophages into M2-type. As a result, it was confirmed that the treatment of gold-containing agents inhibited the expression of α-SMA and iNOS, increased the expressions of TREM-2 and arginase-1, thereby promoting the transformation of macrophages into M2-type while simultaneously inhibiting the transformation into M1-type macrophages (see Examples 3, 4, and 6).

In another exemplary embodiment of the present invention, the inhibition of liver fibrosis by the administration of a gold-containing agent was examined, and as a result, it was confirmed that the treatment with the gold-containing agents apparently lowered the expressions of α-SMA and collagen 1a1, which are activation indices for stellate cells, and also significantly reduced the liver fibrosis score at 10 mg/kg (see Example 5).

Meanwhile, the pharmaceutical composition of the present invention may further contain at least one kind of a known active ingredient, which is effective for the treatment of liver fibrosis or liver cirrhosis, along with the gold-containing agent.

The composition of the present invention may further contain an appropriate carrier, excipient, and diluent which are conventionally used in the preparation of pharmaceutical compositions. Additionally, the composition of the present invention may be prepared into oral formulations such as powders, granules, tablets, capsules, suspensions, emulsions, syrups, aerosols, etc., formulations for external use, suppositories, and sterile injections, and may preferably be prepared into unit dosage forms suitable for oral administration, according to the conventional method.

The carriers, excipients, and diluents to be contained in the composition of the present invention may include: lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, mineral oil, etc. For formulation of the composition, commonly-used diluents or excipients such as fillers, extenders, binders, humectants, disintegrants, surfactants, etc., may be used.

Solid formulations for oral administration may include tablets, pills, powders, granules, capsules, etc. The solid formulations may be prepared by adding at least one excipient, e.g., starch, calcium carbonate, sucrose or lactose, gelatin, etc. Additionally, lubricants such as magnesium stearate, talc, etc., may be used in addition to simple excipients. Examples of liquid formulations for oral administration may include suspensions, formulations for internal use, emulsions, syrups, etc., and various kinds of excipients, e.g., humectants, sweeteners, fragrances, preservatives, etc., may be used in addition to simple diluents such as water and liquid paraffin. Formulations for parenteral administration may include sterile aqueous solutions, non-aqueous solvents, suspensions, emulsions, lyophilized preparations, and suppositories. For non-aqueous solvents and suspensions, propylene glycol, polyethylene glycol, a vegetable oil such as olive oil, and an injectable ester such as ethyl oleate may be used. Examples of bases for suppositories may include Witepsol, macrogol, Tween 61, cacao butter, laurin butter, glycerogelatin, etc.

The composition according to the present invention is administered in a pharmaceutically effective amount. As used herein, the term "pharmaceutically effective amount" refers to an amount sufficient for the treatment of diseases at a reasonable benefit/risk ratio applicable to a medical treatment, and the level of the effective dose may be determined based on the factors including the kind of a disease of a subject, severity of illness, drug activity, drug sensitivity, administration time, administration route and excretion rate, length of treatment, factors including drug(s) to be concurrently used in combination, and other factors well-known in the medical field. The composition of the present invention may be administered as an individual therapeutic agent, in combination with other therapeutic agents, or sequentially or simultaneously with a conventional therapeutic agent(s), and may be administered once or multiple times. It is important to administer an amount to obtain the maximum effect with a minimum amount without adverse effects considering the factors described above, and the amount can easily be determined by one of ordinary skill in the art.

Specifically, the pharmaceutically effective amount of the pharmaceutical composition according to the present invention may vary depending on the age, sex, health conditions, body weight of a patient, absorption rate of active ingredients in vivo, inactivation rate and excretion rate, the kind of the disease, and drug(s) administered in combination, generally in an amount of about 0.01 mg/kg/day to about 100 mg/kg/day, preferably in an amount of about 0.1 mg/kg/day to about 30 mg/kg/day, and may be administered once daily or in a few divided doses.

The pharmaceutical composition of the present invention may be administered to a subject via various routes. All the modes of administration may be expected, for example, the pharmaceutical composition of the present invention may be administered by oral, rectal or intravenous, intramuscular, subcutaneous, intrauterine epidural, or intracerebrovascular injections. The pharmaceutical composition of the present invention may be determined according to the kind of drugs (active ingredients) along with various factors such as the disease to be treated, administration route, age, sex, body weight of a patient, severity of the disease, etc.

In another aspect, the present invention provides a method for treating liver fibrosis or liver cirrhosis, which includes administering the pharmaceutical composition to a subject. As used herein, the term "subject" refers to an object which requires treatment of a disease, and more specifically, mammals such as humans, non-human primates, mice, rats, dogs, cats, horses, cattle, etc.

Furthermore, in still another aspect, the present invention provides a health functional food composition for preventing or ameliorating liver fibrosis or liver cirrhosis including a gold-containing agent as an active ingredient.

As used herein, the term "amelioration" refers to all of the actions by which the parameters associated with the conditions under treatment, for example, the symptoms, are at least lessened. In particular, the functional food composition may be used for preventing or ameliorating liver fibrosis or liver cirrhosis simultaneously in combination with or separately from the pharmaceutical drug for treatment, before or after the occurrence of the subject disease.

The kinds of the food are not particularly limited. Examples of the food, in which the active ingredients can be added, may include drinks, meats, sausages, breads, biscuits, rice cakes, chocolates, candies, snacks, cookies, pizzas, ramens, other noodles, gums, dairy products including ice cream, various kinds of soups, beverages, alcoholic beverages, vitamin complexes, milk products, processed milk products, etc., and may include all kinds of health functional foods from the conventional point of view.

In the health functional food composition of the present invention, the active ingredients may be added as they are into the food, may be used along with other foods or food ingredients, or may be appropriately used according to the conventional method. The mixed amount of the active ingredients may be appropriately determined according to the intended use (prevention or amelioration). Generally, in the preparation of foods or beverages, the composition of the present invention may be added in an amount of 15 wt % or less, and preferably in an amount of 10 wt % or less. However, in a case of a long-term intake of the food for the purpose of health and hygiene or for health control, the amount of the composition may be less than the above range.

With respect to the health functional food composition of the present invention, there is no particular limitation on other ingredients except that the active ingredients described above are contained as essential ingredients, and various kinds of flavoring agents or natural carbohydrates, etc., may be contained as additional ingredient(s) as in the conventional beverages. Examples of the natural carbohydrates may include conventional saccharides such as monosaccharides (e.g., glucose, fructose, etc.), disaccharides (e.g., maltose, sucrose, etc.), and polysaccharides (e.g., dextrin, cyclodextrin, etc.); and sugar alcohols such as xylitol, sorbitol, erythritol, etc. As flavoring agents other than those described above, natural flavoring agents (taumatin, stevia extracts (e.g., rebaudioside A, glycyrrhizin, etc.)) and synthetic flavoring agents (saccharin, aspartame, etc.) may be advantageously used. The percentage of the natural carbohydrates may be appropriately determined by one of ordinary skill in the art.

Additionally, the health functional food composition of the present invention may include a variety of nutrients, vitamins, minerals (electrolytes), synthetic and/or natural flavoring agents, colorants and fillers (cheese, chocolate, etc.), pectic acid or salts thereof, alginic acid or salts thereof, organic acids, protective colloidal thickening agents, pH modifiers, stabilizers, preservatives, glycerin, alcohols, carbonating agents used in carbonated beverages, etc. These ingredients may be used independently or in combination. The percentage of these additives may also be appropriately selected by one of ordinary skill in the art.

Hereinafter, the present invention will be described in more detail with reference to the following Examples. However, these Examples are for illustrative purposes only, and the invention is not intended to be limited by these Examples.

EXAMPLE 1

Experimental Preparation and Methods 1-1. Experimental Preparation

A. Preparation of Liver Tissue from a Human Liver Fibrosis Patient

Human liver tissues, both normal tissues and the tissues with liver fibrosis, isolated from liver cancer tissues of 36 cases were used after obtaining the clinical test approval (CHOSUN 2013-04-005) by Department of Pathology, School of Medicine, Chosun University.

B. Preparation of a Mouse Model with Carbon Tetrachloride-Induced Liver Fibrosis A mouse model with carbon tetrachloride-induced liver fibrosis was prepared by repeatedly administering 0.5 ml/kg of carbon tetrachloride to C57BL/6J mice twice a week for three weeks.

1-2. Experimental Methods

A. Western blot

Sodium dodecyl sulfate-polyacrylamide gel electrophoresis (SDS-PAGE) was performed using a gel electrophoresis apparatus (Mighty Small SE 250, Hoefer Scientific Instruments, San Francisco, USA) according to the Laemmli's protocol. A dissolved fraction of cells was diluted in a sample dilution buffer [63 mM Tris (pH.6.8), 10% glycerol, 2% SDS, 0.0013% bromophenol blue, 5% β-mercaptoethanol) and electrophoresed in an electrode buffer (containing Tris (15 g), glycerin (72 g), and SDS (5 g) in 1L solution) using 8%- and 10% gels. Upon completion of gel electrophoresis, the gel was transferred onto a nitrocellulose membrane at 40 mAmps for 3 hours in a transfer buffer solution (25 mM Tris, 192 mM glycerin, 20% v/v methanol (pH 8.3)). Each of anti-TREM-2, anti-arginase-1, anti-iNOS, anti-α-SMA, and anti-collagen-1a1, as primary antibodies, was reacted on the nitrocellulose membrane, respectively, and horseradish peroxidase-conjugated goat anti-rabbit IgG and horseradish peroxidase-conjugated goat anti-mouse IgG, as secondary antibodies, were reacted thereonto for 1 hour, and the nitrocellulose membrane was allowed to develop colors using the ECL detection system (ECL chemiluminescence system, Amersham, Gaithesberg, Mass., USA). The identity of protein contents in a sample was confirmed using anti-β-actin antibody and anti-lamin A/C. With respect to the change in the amount of protein expression, the coloration intensity was induced using a densitometry and the scanning of the densitometry was performed using the Image Scan & Analysis System, Alpha-Innotech Co. (USA). In each lane, the intensities were calculated using the AlphaEase™ version 5.5 software by subtracting background intensities.

In the case of liver tissue, a certain amount of liver tissue was homogenized in a mortar along with liquid nitrogen and a cell lysis buffer, transferred into a new tube, and vortexed. The resultant was centrifuged at 14,000 rpm and 4° C. for 20 minutes and the middle layer was collected therefrom and the protein amount was quantitated by Bradford assay. After subjecting 30 μg of the protein to electrophoresis by SDS-PAGE, the change in the expression of α-SMA protein was measured by western blot analysis.

B. Evaluation of Fibrosis Scores

The evaluation of fibrosis scores was performed by a resident doctor specialized on pathology under microscopic examination of at least 10 parts by weight of each tissue sample via a double blind test. The standard guidelines are as follows; Stage 0: none; Stage 1: Enlarged, fibrotic portal areas; Stage 2: Periportal or portal-portal septa but intact architecture; Stage 3: Fibrosis with architectural distortion but no obvious cirrhosis; Stage 4: Probable or definite cirrhosis.

EXAMPLE 2

Confirmation of Inhibition of Liver Fibrosis by TREM-2, which is a Macrophage M2 Marker 2-1. Confirmation of the Increase/Decrease of TREM-2 Expression in Tissues with Liver Fibrosis The increase/decrease of TREM-2 (i.e., a macrophage M2 marker) expression was confirmed in tissues isolated from a patient with liver fibrosis and a mouse with carbon tetrachloride-induced liver fibrosis in Example 1-1 by western blot analysis, and the results are shown in FIG. 3a.

Figure 3A:
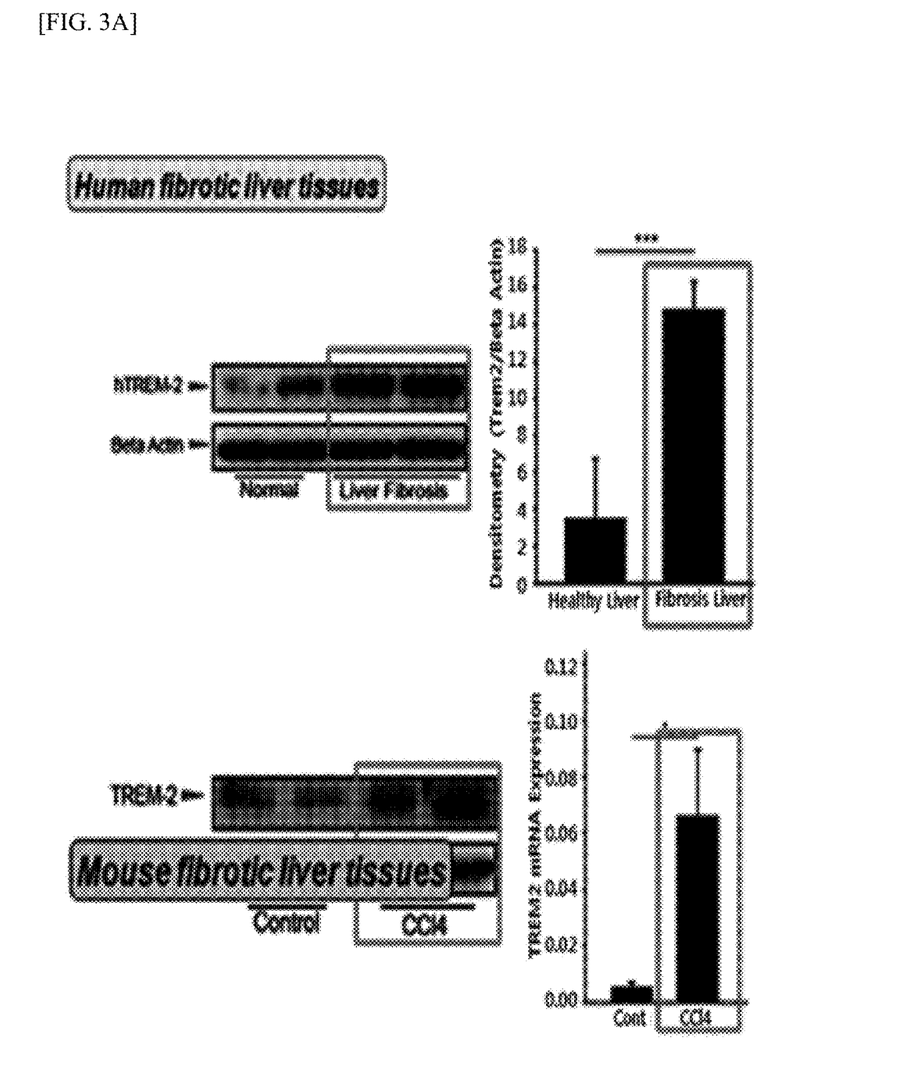
FIG. 3a shows the results confirming the increase/decrease of the expression of TREM-2, which is an M2-type macrophage marker, in the liver tissues isolated from a human liver fibrosis patient and a mouse model with carbon tetrachloride (CC14)-induced liver fibrosis.

As shown in FIG. 3a, it was confirmed that the TREM-2 (i.e., a macrophage M2 marker) expression was significantly increased in the tissues isolated from the patient with liver fibrosis and the mouse with carbon tetrachloride-induced liver fibrosis.

2-2. Confirmation of Inhibition of Liver Fibrosis by TREM-2

The release of collagen (a causative material of liver fibrosis), transforming growth factor-β (TGF-β (a core factor for fibrosis), etc.), contributes to the activation of hepatic stellate cells.

In this regard, mouse embryonic fibroblasts (MEF) having a characteristic similar to active stellate cells were treated with the medium obtained from the macrophages, where TREM-2 was overexpressed, and the increase/decrease in expressions of alpha-smooth muscle actin (α-SMA, a protein specific to stellate cells differentiated into a fibroblast type), which is a marker protein widely used as a marker for the activation of stellate cells, and a collagen-1a1 (representative fibrous collagen), was confirmed by western blot analysis. The results are shown in FIG. 3b.

Figure 3B:
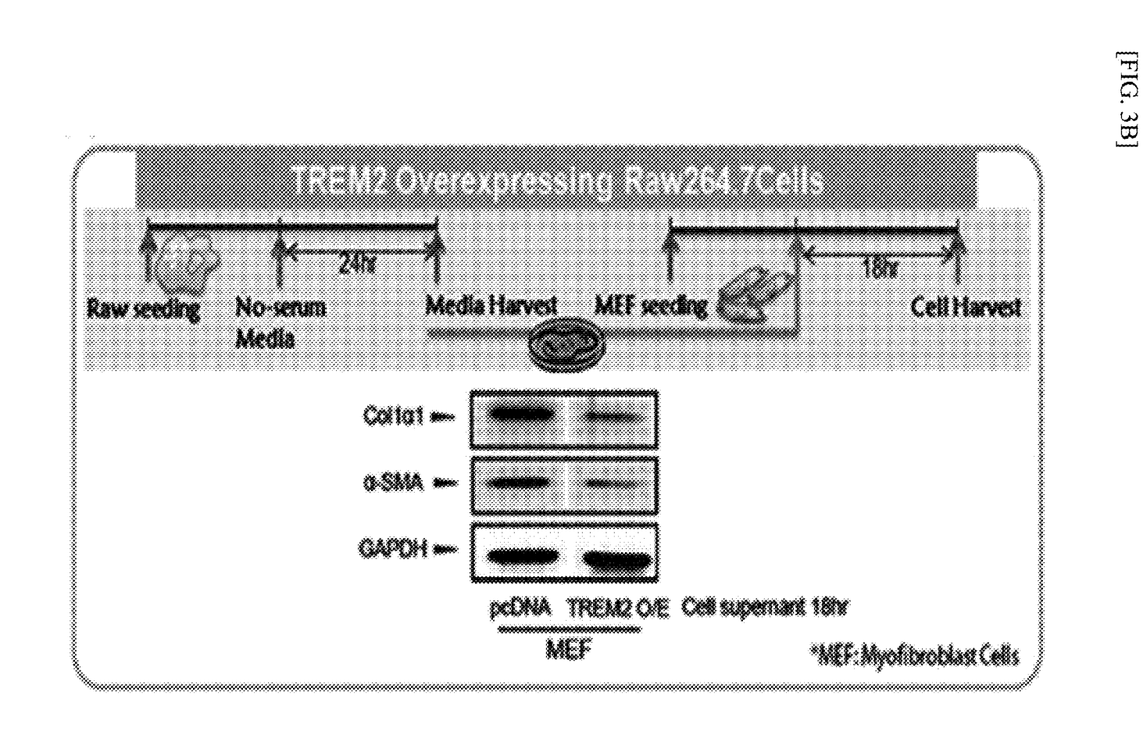
FIG. 3b shows the results confirming the increase/decrease of the expression of α-SMA and collagen-1a1 after treating MEF cells with a culture medium obtained from macrophages, in which TREM-2 was overexpressed.

As shown in FIG. 3b, it was confirmed that the treatment with the medium obtained from the macrophages, where TREM-2 was overexpressed, inhibited the expressions of α-SMA and collagen-1a1. From the above results, it was confirmed that TREM-2 receptor, which is an M2 marker, can effectively inhibit liver fibrosis.

EXAMPLE 3

Confirmation of the Increase in Expression of TREM-2, which is a Macrophage M2 Anti-fibrosis Factor, by Treatment with Gold-containing Agents In order to confirm whether gold-containing agents can induce the transformation into M2-type macrophages, the RAW264.7 cells, which is a mouse macrophage cell line, were treated with lipopolysaccharide (LPS)/interferon-gamma (IFN-γ), followed by treatment with auranofin in a condition for differentiation into M1-type macrophages, and the increase/decrease in expressions of iNOS and TREM-2 was confirmed by western blot analysis. The results are shown in FIG. 4.

Figure 4:
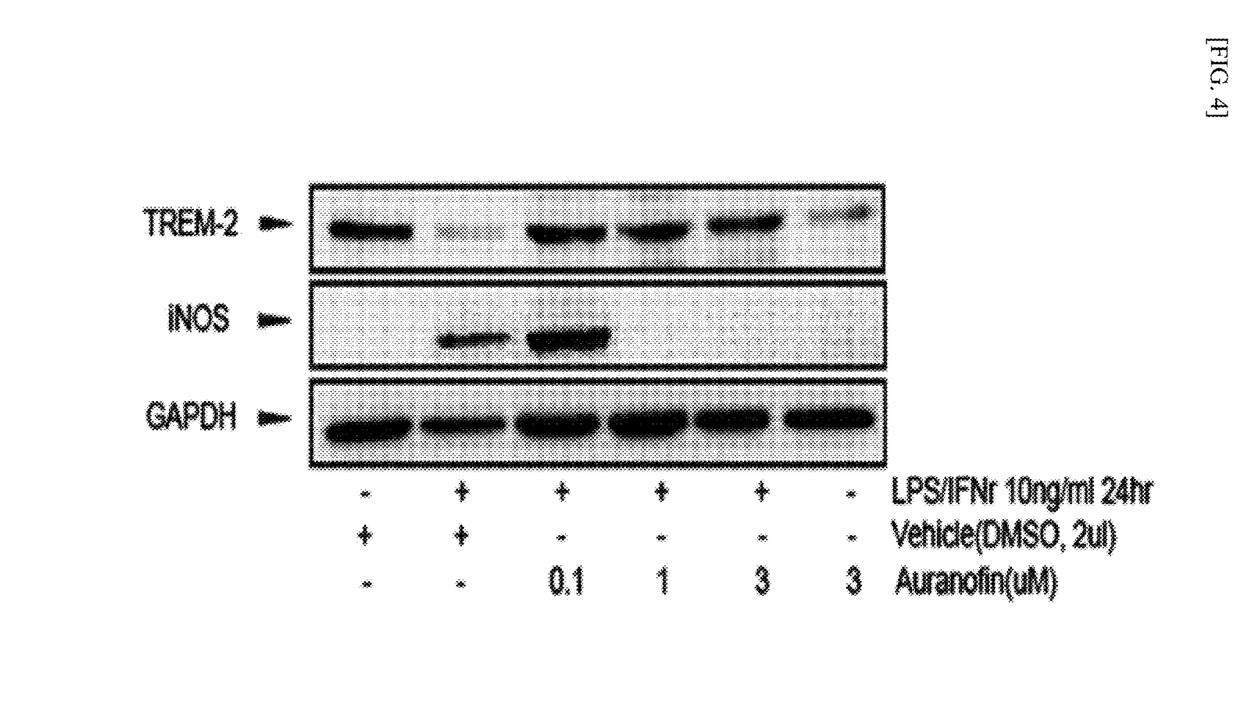
FIG. 4 shows the results confirming the increase/decrease of the expressions of iNOS and TREM-2 after treating RAW264.7 cells with auranofin, in a condition where the RAW264.7 cells are differentiated into M1-type macrophages by treating with LPS/IFN-γ.

As shown in FIG. 4, it was confirmed that the auranofin treatment inhibited the expression of iNOS while increasing the expression of TREM-2. From these results, it was confirmed that gold-containing agents, especially auranofin, can promote the transformation into M2-type macrophages while simultaneously inhibiting the transformation into M1-type.

EXAMPLE 4

Confirmation of the Inhibition of the Activation of Stellate Cells by Exposure of Stellate Cells in the Macrophage Medium Pretreated with Gold-containing Agents The RAW264.7 cells, which is a mouse macrophage cell line, were treated with auranofin and then the medium was treated on the MEF cells having a characteristic similar to that of active stellate cells, and the increase/decrease in expression of α-SMA, which is a marker for activation of stellate cells, was confirmed by western blot analysis. The results are shown in FIG. 5.

Figure 5:
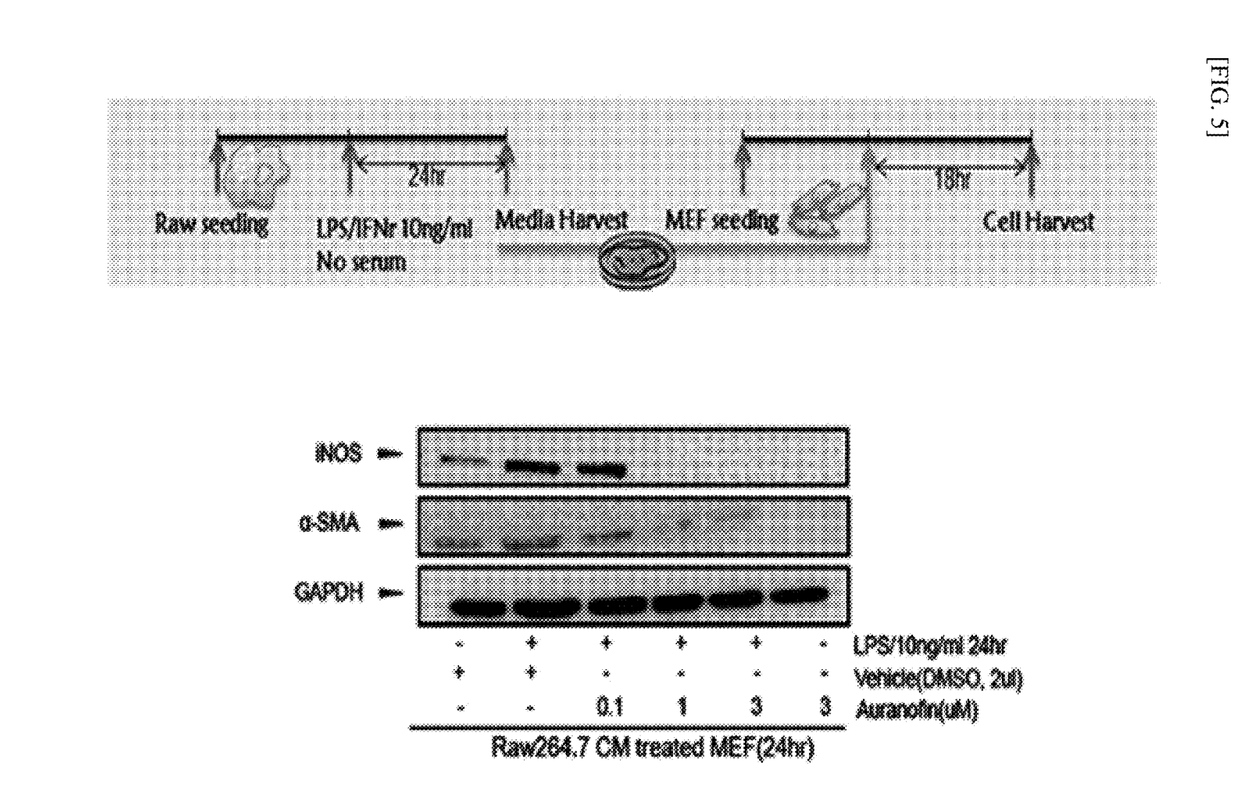
FIG. 5 shows the results confirming the increase/decrease of the expression of α-SMA by treating MEF cells with a culture medium, after treating RAW264.7 cells with auranofin.

As shown in FIG. 5, it was confirmed that the auranofin treatment inhibited the expression of α-SMA. From the above result, it was confirmed that gold-containing agents, especially auranofin, can inhibit the activation of stellate cells by promoting the transformation into M2-type macrophages and increasing the expression of TREM-2.

EXAMPLE 5

Confirmation of Inhibition of Liver Fibrosis by Administration of Gold-containing Agents A mouse model with carbon tetrachloride-induced liver fibrosis prepared in Example 1-1 was orally administered with auranofin in an amount 1, 3, and 10 mg/kg, which are the doses known to be effective for the treatment of arthritis, 5 times a week for 3 weeks. Upon termination of the administration, the liver tissues were subjected to H & E staining for the evaluation of fibrosis scores and some of the liver tissues were crushed for the quantification of α-SMA (an activation index for stellate cells) and collagen-1a1 (an index for collagen accumulation). The results are shown in FIG. 6.

Figure 6:
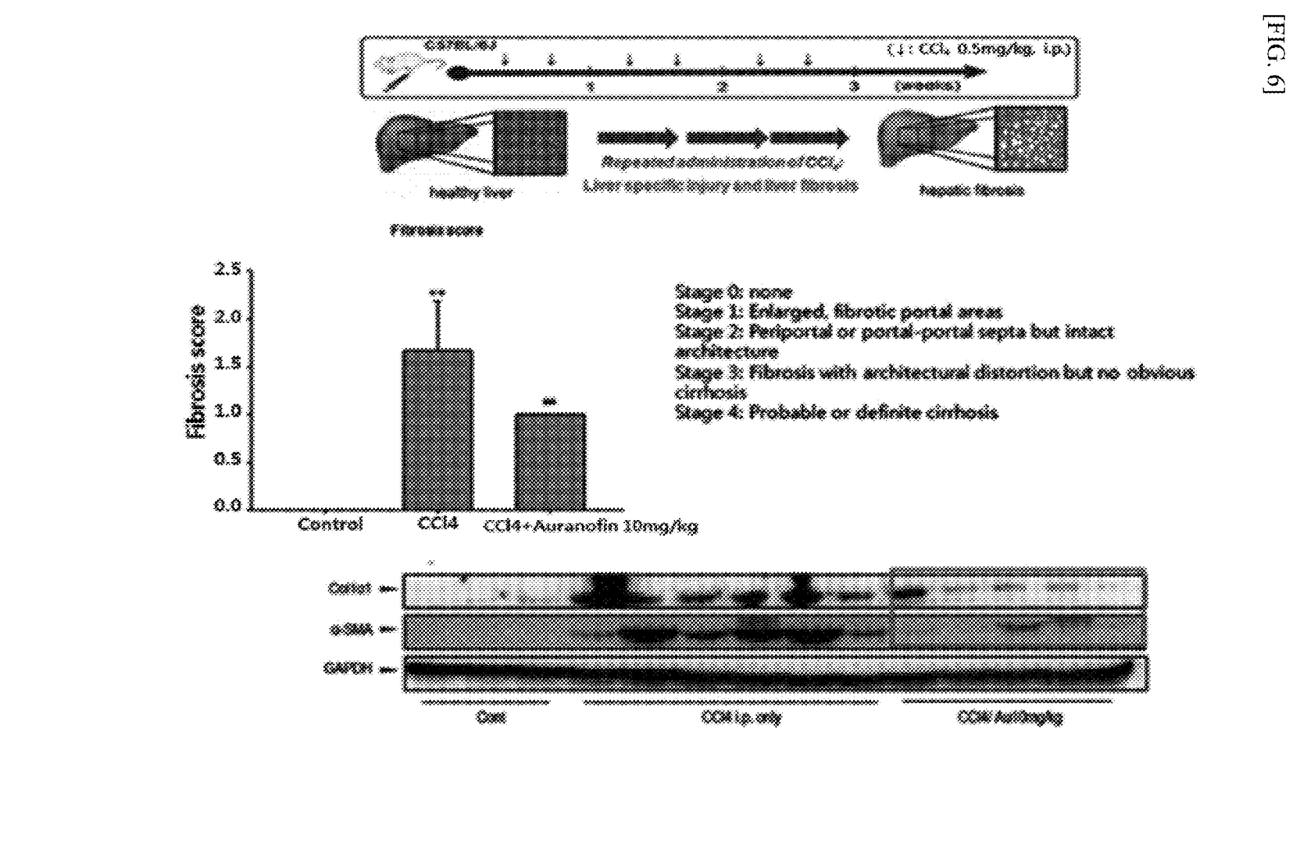
FIG. 6 shows the evaluation results of fibrosis scores of liver tissue after treating a carbon tetrachloride-induced mouse model having liver fibrosis with auranofin followed by H&E staining; and the quantification results of α-SMA and collagen-1a1 of some of the liver tissue after pulverization.

As shown in FIG. 6, it was confirmed that the auranofin treatment apparently reduced the expressions of α-SMA and collagen-1a1, which are indices for the activation of stellate cells, and also significantly lowered the actual liver fibrosis scores at 10 mg/kg.

EXAMPLE 6

Confirmation of the Effects of Inhibiting the Transformation of Macrophages into M1-type and Promoting the Transformation of Macrophages into M2-type by Treatment with Gold-containing Agents The effects of inhibiting the transformation of macrophages into M1-type and promoting the transformation of macrophages into M2-type by treatment with gold-containing agents other than auranofin were additionally confirmed.

First, the RAW264.7 cells, which is a mouse macrophage cell line, were respectively treated with sodium aurothiomalate and aurothioglucose, which are analogous to auranofin, in a condition for differentiating the cells into M1-type macrophages by treating with lipopolysaccharide (LPS)/interferon-gamma (IFN-gamma), and the increase/decrease in expression of iNOS was confirmed by western blot analysis.

Figure 7A:
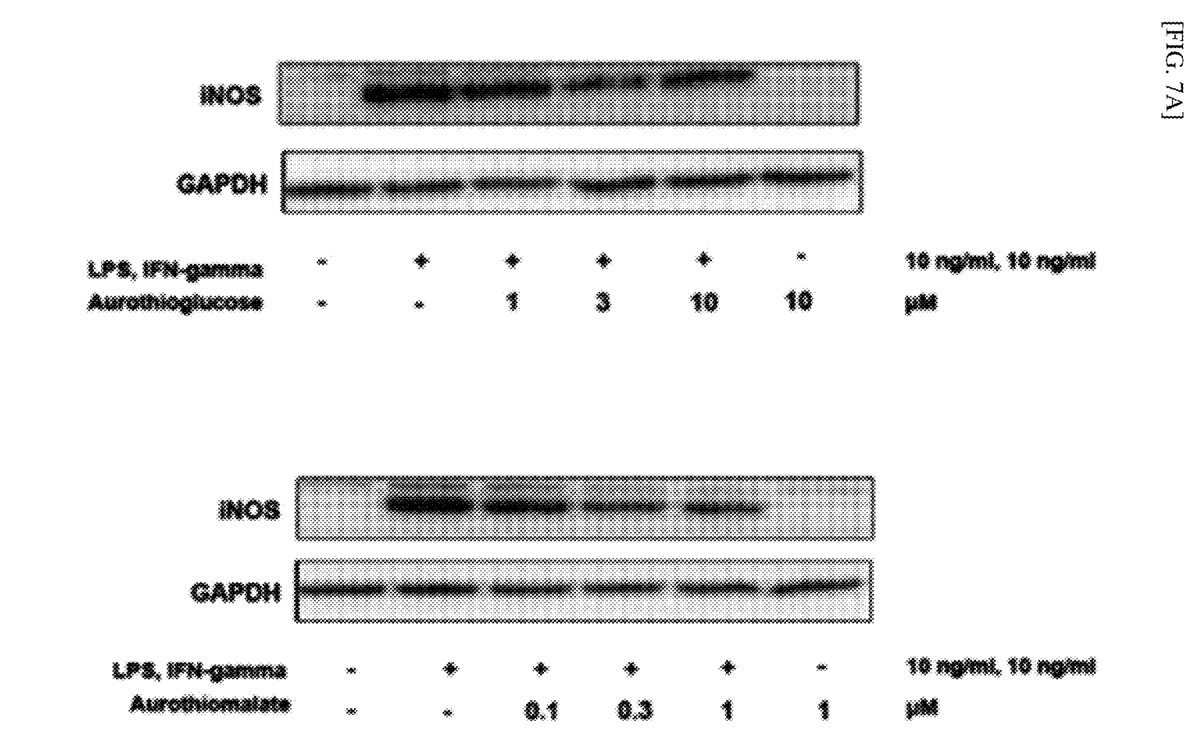
FIG. 7a shows the results confirming the increase/decrease of the expression of iNOS after treating RAW264.7 cells with sodium aurothiomalate and aurothioglucose, respectively, in a condition where the RAW264.7 cells are differentiated into M1-type macrophages by treating with LPS/IFN-γ.

As a result, as shown in FIG. 7a, it was confirmed that the treatments with sodium aurothiomalate and aurothioglucose inhibited the expression of iNOS.

Additionally, the RAW264.7 cells, which is a mouse macrophage cell line, were respectively treated with sodium aurothiomalate and aurothioglucose, which are analogous to auranofin, in a condition for differentiating the cells into M2-type macrophages by treating with IL-4, and the increase/decrease in expression of arginase-1 was confirmed by western blot analysis.

Figure 7B:
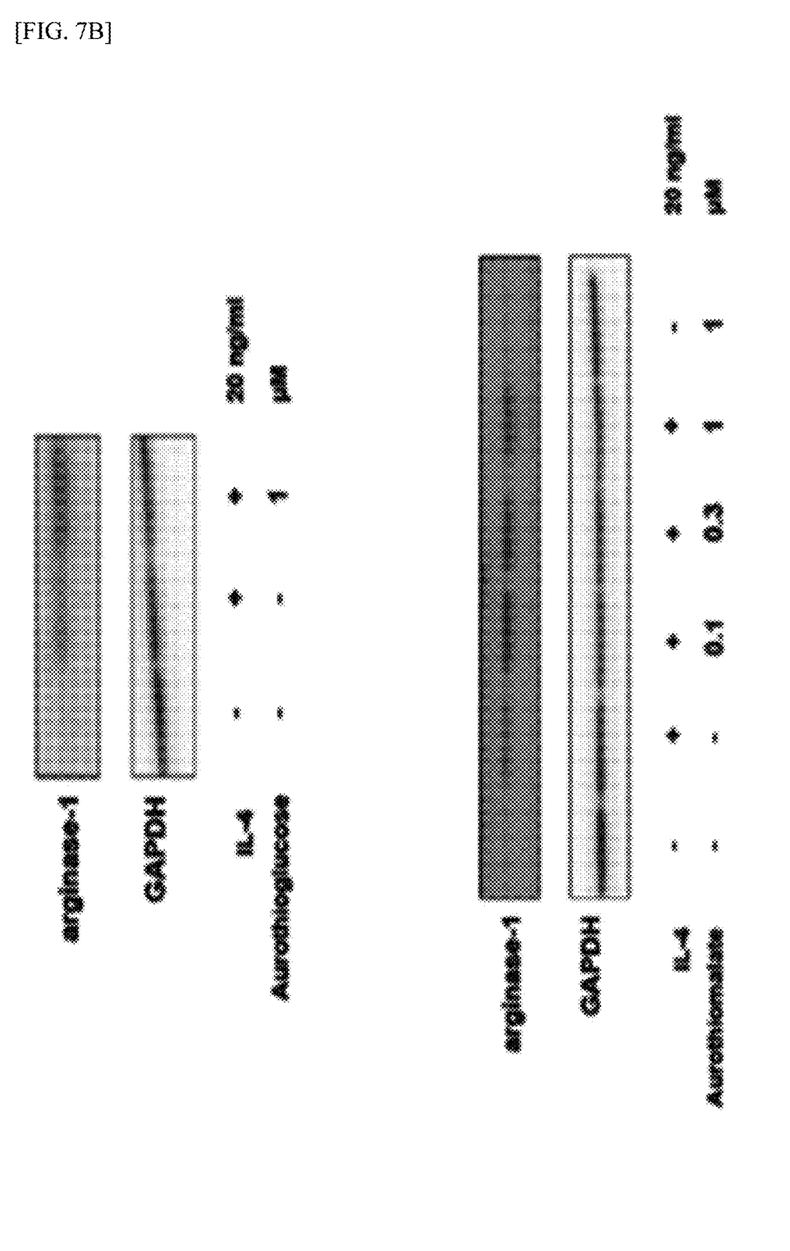
FIG. 7b shows the results confirming the increase/decrease of the expression of arginase-1 after treating RAW264.7 cells with sodium aurothiomalate and aurothioglucose, respectively, in a condition where the RAW264.7 cells are differentiated into M2-type macrophages by treating with IL-4.

As a result, as shown in FIG. 7b, it was confirmed that the treatments with sodium aurothiomalate and aurothioglucose increased the expression of arginase-1.

From the above results, it was confirmed that gold-containing agents can inhibit the transformation of macrophages into M1-type while simultaneously promoting the transformation of macrophages into M2-type.

The foregoing explanations are provided for illustrative purposes, and a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention.

The composition according to the present invention can not only promote the transformation of macrophages into M2-type but also inhibit the activation of stellate cells due to the increase in TREM-2 expression. Therefore, the composition according to the present invention is expected to be effectively used as a pharmaceutical composition, a food composition, etc., for preventing, treating, or ameliorating liver fibrosis or liver cirrhosis.

What is claimed is:
1. A method for treating liver fibrosis comprising administering a gold-containing agent selected from the group consisting of auranofin, sodium aurothiomalate, aurothioglucose, sodium aurothiosulfate, and disodium aurothiomalate to a subject which requires treatment of liver fibrosis, orally in a pharmaceutically effective amount for the treatment thereof.

2. The method of claim 1, wherein the gold containing agent is auranofin.

\* \* \* \* \*